(12) United States Patent
Adelsheim

(10) Patent No.: US 11,766,575 B2
(45) Date of Patent: Sep. 26, 2023

(54) QUALITY ASSURANCE PROCESS FOR RADIATION THERAPY TREATMENT PLANNING

(71) Applicant: Varian Medical Systems, Inc., Palo Alto, CA (US)

(72) Inventor: Charles Adelsheim, Mountain View, CA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 1057 days.

(21) Appl. No.: 16/449,450

(22) Filed: Jun. 24, 2019

(65) Prior Publication Data

US 2020/0398083 A1 Dec. 24, 2020

(51) Int. Cl.
*G16H 20/40* (2018.01)
*A61N 5/10* (2006.01)

(52) U.S. Cl.
CPC ......... *A61N 5/1075* (2013.01); *A61N 5/1071* (2013.01); *G16H 20/40* (2018.01); *A61N 5/1031* (2013.01); *A61N 5/1039* (2013.01); *A61N 5/1064* (2013.01); *A61N 2005/1074* (2013.01)

(58) Field of Classification Search
CPC .. A61N 5/1075; A61N 5/1071; A61N 5/1031; A61N 5/1039; A61N 5/1064; A61N 2005/1074; A61N 5/103; A61N 2005/1041; G16H 20/40; G16H 40/20; G06N 3/0472; G06N 3/08; G06N 3/0454
See application file for complete search history.

(56) References Cited

U.S. PATENT DOCUMENTS

| | | | |
|---|---|---|---|
| 2009/0187867 A1* | 7/2009 | Lawrence | G06F 30/398 716/136 |
| 2017/0076246 A1* | 3/2017 | Volkov | G06N 5/04 |
| 2017/0330099 A1* | 11/2017 | de Vial | G06Q 40/04 |
| 2019/0173918 A1* | 6/2019 | Sites | G06N 3/084 |
| 2019/0354489 A1* | 11/2019 | Gupta | G06N 3/084 |
| 2020/0193153 A1* | 6/2020 | Lee | G06V 30/418 |

FOREIGN PATENT DOCUMENTS

WO 2019047795 A1 3/2019

OTHER PUBLICATIONS

Jarrett (NPL—Applications and limitations of machine learning in radiation oncology, Daniel Jarrett, May 19, 2019) (Year: 2019).*
International Search Report and Written Opinion of the International Searching Authority, International application No. PCT/US2020/038868, dated Oct. 13, 2020.

(Continued)

*Primary Examiner* — Michael A Keller
(74) *Attorney, Agent, or Firm* — SU IP CONSULTING

(57) ABSTRACT

A method enables testing and evaluation of an expert human reviewer or an artificial intelligence (AI) error detection engine associated with a radiotherapy treatment planning process. Intentional errors are introduced into the output of a software module or AI engine that performs a certain step in the radiotherapy treatment planning process. The efficacy of the human or AI reviewer in detecting errors can then be evaluated or tested by determining whether the human or AI reviewer has detected the introduced error.

20 Claims, 6 Drawing Sheets

(56) References Cited

OTHER PUBLICATIONS

Daniel Jarrett et al., "Applications and limitations of machine learning in radiation oncology", Br J Radiol, 2019, Retrieved from the Internet at URL<https://doi.org/10.1259/bjr.20190001>. Retrieved on Mar. 24, 2021.

Ling Huang et al., "Adversarial machine learning", In Proceedings of 4th ACM Workshop on Artificial Intelligence and Security, Oct. 2011, pp. 43-58.

Kunfeng Wang et al., "Generative Adversarial Networks: Introduction and Outlook", IEEE/CAA Journal of Automatica Sinica, Oct. 2017, pp. 588-598, vol. 4, No. 4.

\* cited by examiner

QUALITY ASSURANCE PROCESS FOR RADIATION THERAPY TREATMENT PLANNING

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on a planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated and an appropriate treatment plan generated and planning target volume determined.

Due to the geometric complexities in applying a radiation treatment to a three-dimensional target that can be in close proximity to one or more organs at risk, treatment planning is a complex process that can involve the participation of multiple highly trained medical professionals and analysis using sophisticated software. As a result, generation of a treatment plan that correctly doses a gross tumor volume without excessively dosing nearby organs at risk is a multi-step process, where each step can be time-consuming and often can only be performed by expert personnel. Furthermore, because many steps in the treatment planning process may include subjective assessments and judgment calls, details of a particular treatment plan may vary based on the specific personnel who participated in the treatment planning process.

SUMMARY

In accordance with at least some embodiments of the present disclosure, a method for quality assurance (QA) testing of a radiotherapy treatment planning process enables testing and evaluation of an expert human reviewer or an artificial intelligence (AI) error detection engine. Specifically, intentional errors are introduced into the output of a software module or AI engine, referred to hereinafter as the "reviewed module," that performs a certain step in a radiotherapy treatment planning process. The efficacy of the human or AI reviewer in detecting errors can then be evaluated or tested by determining whether the human or AI reviewer has detected the introduced error. In some embodiments, such a determination is made based on an error check response from the reviewer, such as an error detection output from an AI engine reviewer or a user input made by a human reviewer.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
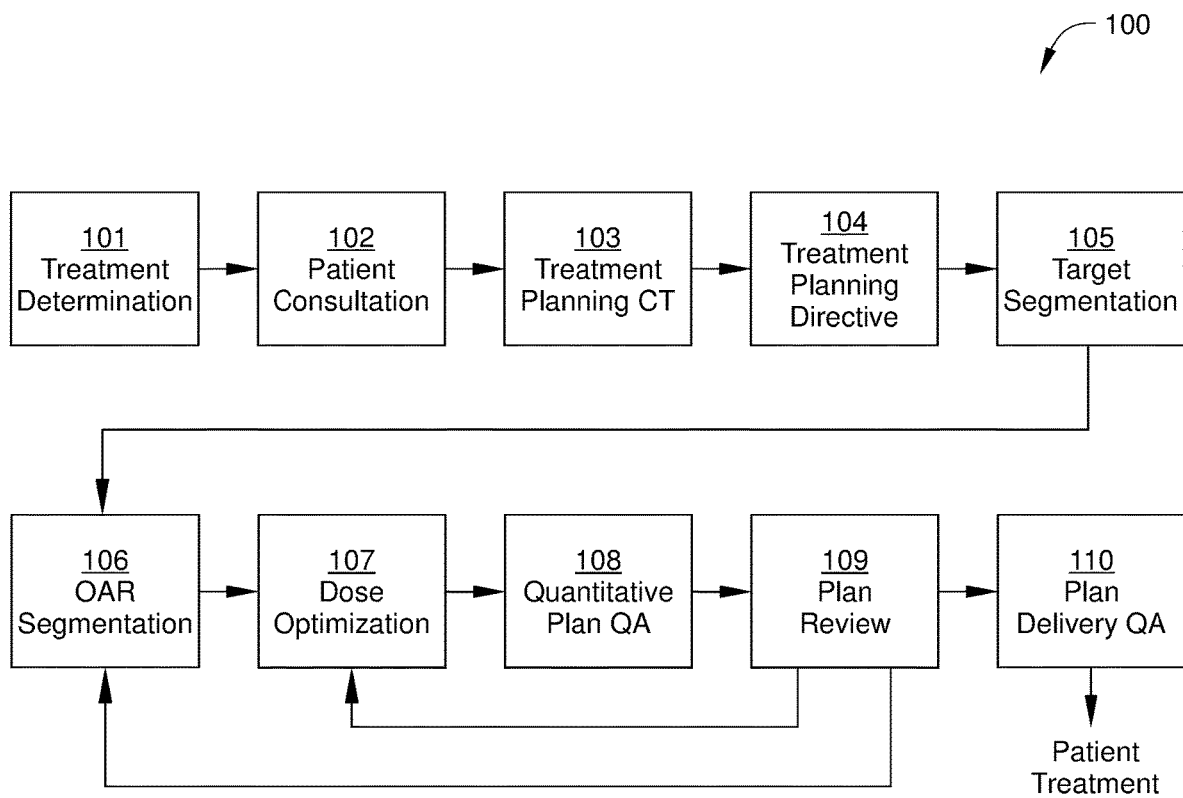
FIG. 1 is a block diagram illustrating an example treatment planning process 100.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As noted above, the process of treatment planning for a particular patient is a multi-step process that can include analysis performed by both expert personnel and sophisticated software applications. One exemplary treatment planning process is illustrated in FIG. 1.

FIG. 1 is a block diagram illustrating an example treatment planning process 100. Treatment planning process 100 includes a plurality of steps 101-110 that are performed to generate a treatment plan for a particular patient. Treatment planning process 100 is performed in response to a diagnosis for a patient that indicates the patient is to be treated via external beam radiation therapy. The diagnosis typically indicates external beam radiation therapy (instead of internal radiation therapy) based on various factors, including: the type of cancer tumor that has been detected, the size of the detected tumor, the location of the tumor in the body, proximity of the tumor to organs at risk (OARs) or other normal tissues that are sensitive to radiation, the general health and medical history of the patient, the presence of other types of cancer in the patient, the age of the patient, certain medical conditions of the patient, and the like.

As shown, treatment planning process 100 includes one or more of the following steps: a treatment determination step 101, a patient consultation step 102, a treatment planning computerized tomography (CT) step 103, a treatment planning directive step 104, a target segmentation step 105, an OAR segmentation step 106, a plan optimization step 107, a quantitative plan quality assurance (QA) step 108, a plan review and approval step 109, and a plan delivery QA step 110. As described in greater detail below, some of steps 101-110 are performed by a suitably trained medical professional, some of steps 101-110 are completed by a suitably trained medical profession performing certain software-based analysis, and, in some instances, one or more of steps 101-110 may be performed entirely by a suitably designed software application.

In treatment determination step 101, patient imaging, tumor pathology, and diagnosis for the patient is reviewed, and one or more possible treatment approaches or prescriptions for radiation therapy are determined. In some instances, step 101 is performed by a radiation oncologist, who may be employed at the clinical location where the radiation therapy will ultimately take place. In some instances, the radiation oncologist can be assisted by a software application configured to generate possible treatment approaches based on the diagnosis and imaging information for the patient. In such instances, the radiation oncologist selects and/or modifies one or more of the treatment approaches offered by the software application.

In patient consultation step 102, the radiation oncologist consults with the patient about potential treatment options. As noted in treatment determination step 101, in some instances, one or more of the potential treatment approaches may be selected and/or modified by the radiation oncologist from one or more treatment approaches that are initially proposed by a software application.

In treatment planning CT step 103, a treatment planning CT is specified and performed that shows the tumor and a region of anatomy around the tumor. There is typically an inherent trade-off between image quality/noise level in the treatment planning CT and the radiation dose received by the patient during the treatment planning CT. Thus, in some instances, in step 103, certain parameters of the treatment planning CT scan are manipulated to optimize safer imaging of the patient while maintaining sufficient diagnostic image quality, such as X-ray detector configuration, tube current, tube potential, what reconstruction algorithm is to be employed, patient positioning, scan range, thickness of reconstructed slices, and the like.

In some instances, the radiation oncologist specifies some or all of the parameters of the treatment planning CT scan. Alternatively, in some instances, the radiation oncologist can be assisted by a software application configured to specify potential parameters for the treatment planning CT. For example, such software may specify parameters for the treatment planning CT based on the diagnosis, previously acquired imaging information for the patient, and on the specific treatment approach selected in step 102. The treatment planning CT is then generated by scanning the patient, for example during a clinical visit.

In treatment planning directive step 104, a treatment planning directive is generated based on the treatment planning CT. The treatment planning directive typically describes image studies for a treatment site, including target tissue structures and normal tissue structures to be defined via the imaging studies. These target and normal tissue structures are subsequently used for treatment planning. For scoring multiple treatment plans within an optimization process, the treatment planning directive may also specify expansions of the target tissue structures and normal tissue structures. Thus, in addition to the gross tumor volume (GTV), the treatment planning directive may further include clinical target volume (CTV), the internal target volume (ITV), the planning target volume (PTV), OARs, and/or a planning organ at risk volume (PRV), among others. The treatment planning directive may further specify radiation therapy prescription guidelines, planning suggestions, and/or special instructions.

In some instances, the radiation oncologist generates some or all of the treatment planning directive, for example based on local clinical standards, specific medical conditions of the patient, and the like. Alternatively, in some instances, the radiation oncologist can be assisted by a software application configured to suggest some or all of the information included in the treatment planning directive.

In target segmentation step 105, the target of the planned radiation therapy is delineated based on the treatment planning CT and on information included in the treatment planning directive. For example, one or more of the GTV, the CTV, the ITV, and/or the PTV are delineated on two-dimensional slices from the reconstructed volume imaged in the planning treatment CT. In some instances, the radiation oncologist performs one or more of these delineations manually via a display screen. Generally, the radiation oncologist delineates the various target volumes based on visual cues in each two-dimensional slice of the reconstructed volume as well as on personal training and experience. Alternatively, in some instances, the radiation oncologist can be assisted in segmenting the one or more target regions (GTV, CTV, ITV, PTV, etc.) by a software application configured to automatically generate a segmentation of the GTV, the PTV, and the like. Due to the algorithmic complexity of the segmentation process, such software applications may include one or more machine-learning models trained to approximate human logic or decision making while searching for hidden structures, patterns, or features in the two-dimensional slices. In such instances, the radiation oncologist can then review and/or modify such automatically generated segmentations. In some instances, multiple segmentations for a particular target region may be generated by the software application, and the radiation oncologist selects the most appropriate segmentation.

In OAR segmentation step 106, OARs that are defined in the treatment planning directive are delineated (i.e., segmented). In some instances, the radiation oncologist or a dosimetrist performs one or more of the OAR segmentations manually via a display screen. Alternatively, in some instances, an autosegmentation software application configured to automatically segment one or more of the defined OARs can generate some or all of the OAR segmentations, and the radiation oncologist can review and/or modify such segmentations. In such instances, the autosegmentation software application may generate multiple segmentations for a particular OAR based on various factors, including, for example, user inputs, information included in the treatment planning directive (such as clinical margins), and/or other factors. As noted above, due to the algorithmic complexity of the segmentation process, such software applications may include one or more machine-learning models.

In plan optimization step 107, one or more plans for the planned treatment are optimized. That is, one or more beam geometries for implementing the planned treatment is determined and a dose distribution for each beam geometry is optimized. In some instances, a qualified dosimetrist employing a software application determines the one or more beam geometries and optimizes the associated dose distribution, then a physician responsible for the patient typically approves one or more of the plans. In some instances, the software application is approved for such use by the Food and Drug Administration (FDA). Alternatively, in some instances, the software application that includes one or more machine-learning models may generate one or more beam geometries and associated optimized dose distributions in plan optimization step 107, and a dosimetrist may select and/or modify and/or review the output of the software application. Generally, in such instances, physician approval is still required of the plans generated by the FDA-approved software application. Alternatively, in some instances, certain machine-learning software applications may generate a plan that includes a beam geometry and an associated optimized dose distribution without dosimetrist review. However, in such instances, approval by the responsible physician is generally still required.

In quantitative plan QA step 108, one or more of the plans optimized in step 107 are assessed against specified thresholds or other metrics to determine whether each plan meets clinical goals as prescribed in the treatment planning directive. For example, the thresholds may include institution-defined thresholds, physician-defined thresholds, thresholds included in the treatment planning directive, dosing thresholds established for the particular patient, and the like. Each plan assessed in quantitative plan QA step 108 is compared to the above quantitative thresholds. In some instances, the physician responsible for the patient assesses each of the plans approved in plan optimization step 107. In other instances, a machine learning-based software application can be employed to detect and flag plans that exceed one or more of the specified thresholds. In such instances, the physician responsible for the patient only reviews the plans that are flagged.

In plan review and approval step 109, the physician responsible for the patient reviews the available plans and selects the best plan for implementing the treatment prescribed in the treatment planning directive. In some instances, the physician may request changes in the selected plan, in which case GTV segmentation, OAR segmentation step 106, and/or plan optimization step 107 is performed again.

In plan delivery QA step 110, the plan that is reviewed and selected in plan review and approval step 109 is delivered on a suitable radiation therapy system, and a predicted dose is measured. The patient is then treated with the selected plan.

As shown in FIG. 1, radiotherapy treatment planning is a complex process that can involve the participation of multiple highly trained medical professionals and analysis with sophisticated software. To reduce the cost of radiotherapy treatment planning and to enhance uniformity of treatment plans, considerable effort has been made to apply machine learning to the process of radiotherapy planning. Specifically, a properly trained artificial intelligence (AI) engine, neural network, or other machine learning software application can be employed to automatically perform certain radiotherapy planning tasks that are currently accomplished through many hours of human effort. For example, automated segmentation algorithms have been developed for the delineation of OARs and other structures on CT, positron emission tomography (PET), MRI images, or images generated with other imaging modalities, for certain regions of patient anatomy. As a result, OARs can be segmented without a radiation oncologist, dosimetrist, or other physician going through the time-consuming task of manually delineating one or more OARs across a plurality of two-dimensional slices of a reconstructed volume. Furthermore, there are efforts underway to automate other steps in treatment planning process 100 besides automated segmentation of OARs.

However, when fully automated steps are incorporated into radiotherapy treatment planning process 100, there exists a danger that even a robustly trained AI engine or neural network may fail to perform the step correctly for 100% of patients. This may be caused by outliers in the patient population, weaknesses in the AI engine, or other factors. While it may be possible to create automated tools that flag potential outlier cases for human review, given the high-risk nature of radiotherapy treatments, especially hypofractionated radiotherapy delivery, for the foreseeable future patient plans will require final review by an expert human. Such review may be comprehensive, including segmentation, beam trajectory, three-dimensional dose, and the like. As a particular AI engine becomes more robust in performing a step of radiotherapy treatment planning process 100, detectable errors become relatively infrequent. As a result, there is a risk that an expert human reviewer tasked with checking the output of the AI engine can become complacent and fail to detect infrequently occurring or subtle errors.

According to various embodiments, a method for quality assurance (QA) testing of a radiotherapy treatment planning process enables testing and evaluation of an expert human reviewer or an AI error detection engine. Specifically, intentional errors are introduced into the output of a software module or AI engine, referred to hereinafter as the "reviewed module," that performs a certain step in a radiotherapy treatment planning process. The efficacy of the human or AI reviewer in detecting errors can then be evaluated or tested by determining whether the human or AI reviewer has detected the introduced error. In some embodiments, such a determination is made based on an error check response from the reviewer, such as an error detection output from an AI engine reviewer or a user input made by a human reviewer.

Alternatively, according to some embodiments, the method described herein for QA testing of a radiotherapy treatment planning process can be applied to end-to-end checking instead of to the review of a single treatment planning module. Thus, in such embodiments, a physician checking for errors in optimized plans that have gone through a complete treatment planning process 100 can be checked by the QA testing method described herein. Further, in some embodiments, a software-based radiotherapy treatment planning process may generate an optimized radiotherapy plan based on a patient CT, where the software-based radiotherapy treatment planning process generates the optimized plan in a single step rather than in the plurality of steps 101-110 shown in treatment planning process 100. In such embodiments, a physician checking for errors in such optimized plans can be checked by the QA testing method described herein.

In some embodiments, the magnitude, obviousness, and clinical seriousness of the introduced errors may be varied as appropriate. For example, in some embodiments, a magnitude, obviousness, and/or clinical seriousness of an introduced error may be varied based on a current reviewer rating, on certain clinical criteria specific to the current step of treatment planning process 100, etc. In some embodiments, a QA process is configured to implement the QA testing of one or more steps of radiotherapy treatment planning process 100. One such embodiment is described below in conjunction with FIG. 2.

Figure 2:
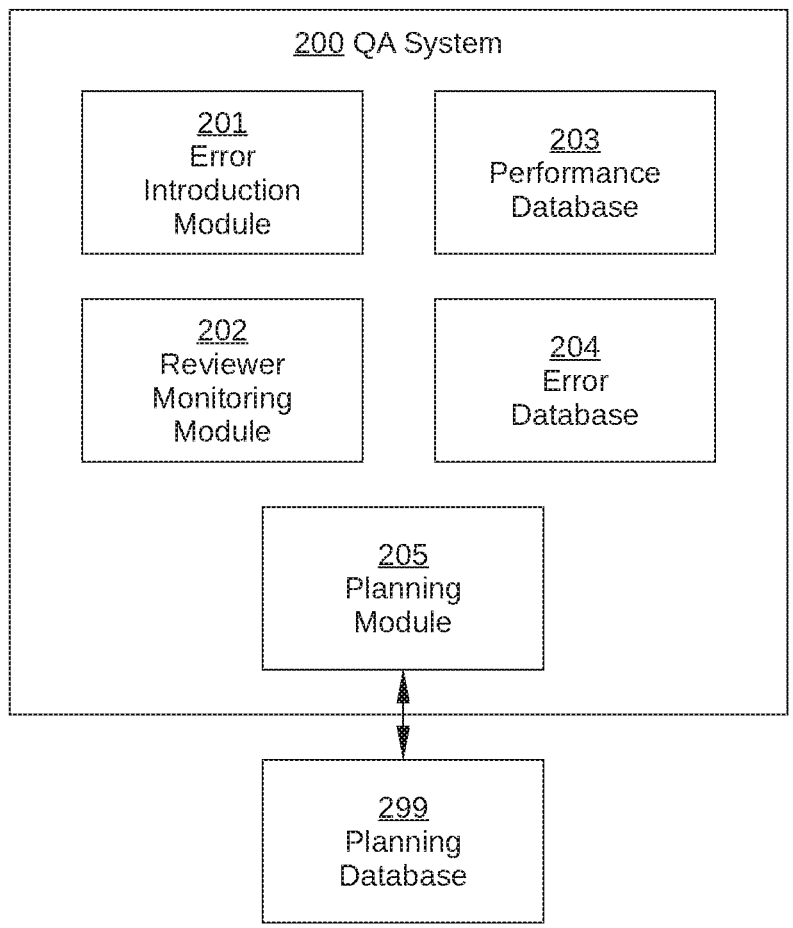
FIG. 2 is a block diagram illustrating a quality assurance process configured to implement one or more embodiments of the present disclosure.

FIG. 2 is a block diagram illustrating a QA system 200 configured to implement one or more embodiments of the present disclosure. QA system 200 can be implemented as a digital tool or other software application that runs on one or more computing devices associated with the execution of one or more of steps 101-110 of treatment planning process 100. For example, in some embodiments, QA system 200 can include a software application running on a computing device that is configured to perform one or more of an automated target segmentation step 105, an automated OAR segmentation step 106, a dose optimization step 107, and the like. Alternatively or additionally, QA system 200 can include a software application running on a computing device that is configured for facilitating an expert human reviewer perform a review of one or more an automated target segmentation step 105, an automated OAR segmentation step 106, a dose optimization step 107, and the like. Alternatively or additionally, QA system 200 can include a software application running on a computing device that is configured to perform an error check or other automated review of one or more steps of treatment planning process 100, for example via a suitably trained AI engine. Thus, QA system 200 can be implemented in a clinical setting or as part of a software-as-service platform that can interface with a plurality of different clinical sites. As shown, in the embodiment illustrated in FIG. 2, QA system 200 includes, without limitation, one or more error introduction modules 201, a reviewer monitoring module 202, a performance database 203, an error database 204, and a planning module 205.

QA system 200 can include one or more error introduction modules 201. Each error introduction module 201 is configured to generate output data for a different one or more of steps 101-110 of treatment planning process 100, where the output data includes at least one error. That is, for a specific reviewed module that performs a step of treatment planning process 100, a corresponding error introduction module 201 is configured to generate output data for that specific reviewed module that includes at least one error.

In some embodiments, an error introduction module 201 is configured to modify output data generated by the corresponding reviewed module, for example by altering one or more specific portions of the output data and/or by adding erroneous information to the output data. Thus, in such embodiments, the error introduction module 201 introduces one or more intentional errors into the output of a specific reviewed module that performs a certain step of treatment planning process 100.

For example, in an embodiment in which an autosegmentation process is performed in target segmentation step 105, one of error introduction modules 201 can be configured to introduce one or more segmentation errors into the output of the autosegmentation process. In such an embodiment, the output of the autosegmentation process may include a segmentation of one or more of a GTV, a CTV, an ITV, and/or a PTV. Thus, in the embodiment, the error introduction module 201 is configured to sufficiently modify or alter one or more such segmentations, so that one or more clinical margins associated with the segmentation(s) are exceeded. For example, in one or more two-dimensional slices of patient anatomy, the boundaries of a GTV segmented by the error introduction module 201 may erroneously encompass too little actual tumor tissue, too much non-tumor tissue, or a combination of both. As a result, radiotherapy based on the one or more modified segmentations can result in a clinically significant degradation of the efficacy of the radiotherapy treatment or of the associated side effects on the patient. Therefore, the introduced modifications to the segmentation(s) are of sufficient magnitude that they should be detected by a reviewer rather than passed to the next step in treatment planning process 100 (e.g., OAR segmentation step 106).

The one or more segmentation errors or modifications introduced into an output segmentation of target segmentation step 105 can include translation, rotation, or other shifting from an original position of an output segmentation. Alternatively or additionally, the one or more segmentation errors or modifications can include distortion of some or all of the output segmentation (e.g., compression or expansion), additions to and/or subtractions from specific segmented regions in the output segmentation, and the like. Alternatively or additionally, the one or more introduced segmentation errors or modifications can be implemented by any other technically feasible programmatic or algorithmic process, such as an AI process or a machine learning process. In alternative embodiments, a generative adversarial network (GAN) can be employed for error generation, as described below in conjunction with FIG. 4.

In some embodiments, one or more segmentation errors or modifications introduced by error introduction module 201 can be selected from error database 204, which includes a plurality of previously generated errors for one or more of steps 101-110. Such previously generated errors can include errors that are associated with a specific step of treatment planning process 100. Furthermore, such previously generated errors can include errors that are tailored to a particular region of patient anatomy, specific scan parameters, a specific X-ray detector configuration, a specific reconstruction algorithm employed for the original CT scan, and the like. Thus, the previously generated errors selected from error database 204 by error introduction module 201 generally correspond to errors typically associated with a specific treatment planning scenario in which error introduction module 201 is being employed. For example, in an embodiment in which radiotherapy treatment planning process 100 is being executed for a pancreatic tumor, the one or more previously generated segmentation errors that are introduced by 201 after target segmentation step 105 can be selected from segmentation errors commonly associated with autosegmentation of the pancreas.

In some embodiments, an error introduction module 201 is configured to generate output data from a particular step of treatment planning process 100 that includes one or more intentional errors. In such embodiments, the error introduction module 201 generates the output data in lieu of the corresponding reviewed module, where the output generated is based on normal input data for the reviewed module. Thus, when a reviewer for a reviewed module of treatment planning process 100 is to be tested, the error introduction module 201 generates output data for the particular step of treatment planning process 100 rather than the reviewed module that normally generates the output data for that step of treatment planning process 100. Further, the one or more intentional errors included in the output data generated by the error introduction module 201 cause one or more clinical margins associated with the output data to be exceeded. As a result, radiotherapy based on the output data generated by the error introduction module 201 can result in a clinically significant degradation of the efficacy of the proposed radiotherapy treatment or increase in patient side effects.

For example, in an embodiment in which an autosegmentation process is performed in target segmentation step 105, one of error introduction modules 201 can be configured to perform that autosegmentation process when a reviewer for the output of target segmentation step 105 is to be tested. Similar to the reviewed module that normally generates the output for target autosegmentation, the error introduction module 201 generates certain output (e.g., one or more of a GTV, a CTV, an ITV, and/or a PTV) based on the normal input to the reviewed module (e.g., CT scans of a region of patient anatomy). However, unlike the reviewed module that normally generates the output for target autosegmentation, the error introduction module 201 generates output that includes one or more intentional errors, such as segmentation errors. In one such embodiment, the error introduction module 201 may include one or more AI engines or other machine-learning models trained to perform autosegmentation of CT images. Such AI engines or machine-learning models are further trained to generate output data that includes one or more errors peculiar to the current step of treatment planning process 100. Further, the one or more errors are configured to be of sufficient magnitude and/or are located such that one or more clinical margins associated with the output of target segmentation step 105 are exceeded. For example, a margin between a GTV and a CTV may be less than is defined in a treatment planning directive associated with the current treatment planning process. In addition, in some embodiments, the AI engines or machine-learning models are trained to generate errors that can be more difficult for a reviewer to detect. A method of training such an AI engine, according to an embodiment, is described below in conjunction with FIG. 4.

Reviewer monitoring module 202 is configured to determine whether an error introduction module 201 is employed after each of steps 101-110 of treatment planning process 100. That is, reviewer monitoring module 202 determines whether the specific reviewer that is responsible for reviewing the module associated with that particular step of treatment planning process 100 is eligible for a QA check. When reviewer monitoring module 202 determines that the reviewer is eligible for a QA check, a suitable error introduction module 201 is then employed to generate output data for that particular step of treatment planning process 100, where the output data includes at least one error. In this way, reviewer monitoring module 202 ensures that each individual reviewer is evaluated or tested with a minimum and maximum frequency. In some embodiments, the frequency of evaluation or testing of a particular reviewer may be automatically adjusted based on the performance of the reviewer during previous evaluation or testing.

In some embodiments, reviewer monitoring module 202 determines the eligibility of a reviewer for a QA check based on a time interval since the specific reviewer has undergone a QA check. Thus, in such embodiments, when the time interval is determined to be exceeded, the reviewer is determined to be eligible for a QA check. Alternatively or additionally, in some embodiments, reviewer monitoring module 202 determines such eligibility based on a number of times since a previous QA check that the reviewer has reviewed the review module. Thus, in such embodiments, when the number exceeds a predetermined threshold value, the reviewer is determined to be eligible for a QA check. Alternatively or additionally, in some embodiments, reviewer monitoring module 202 determines such eligibility based on a current credibility score of the reviewer, which can be stored in performance database 203. Thus, in such embodiments, when the credibility score is less than a predetermined threshold value, the reviewer is determined to be eligible, or more likely to be eligible, for a QA check. Alternatively or additionally, in some embodiments, reviewer monitoring module 202 determines such eligibility based on a random determination process, or any other technically feasible determination process. Thus, in such embodiments, the reviewer may be randomly determined to be eligible for a QA check.

Performance database 203 includes credibility scores or other quantitative measures of the past performance of one or more reviewers. As noted above, a reviewer can be an expert human user or a suitably trained machine-learning entity, such as an AI engine or a neural network. In some embodiments, a reviewer for which performance database 203 stores credibility scores is the radiation oncologist who, in target segmentation step 105, reviews and/or modifies automatically generated segmentations. In some embodiments, such a reviewer is the radiation oncologist who, in OAR segmentation step 106, reviews and/or modifies automatically generated OAR segmentations generated by an AI engine or other software application. In some embodiments, such a reviewer is the physician who approves one or more of the plans generated in plan optimization step 107, where the one or more plans are generated by an FDA-approved software application or by a dosimetrist employing such a software application. In some embodiments, such a reviewer is the dosimetrist who reviews the output of such a software application in plan optimization step 107. In some embodiments, such a reviewer is the physician who performs quantitative plan QA step 108 and assesses plans approved in plan optimization step 107. In some embodiments, a reviewer for which performance database 203 stores credibility scores is an AI engine, neural network, or other machine-learning entity trained to perform any of the above-described review processes in target segmentation step 105, OAR segmentation step 106, plan optimization step 107, or quantitative plan QA step 108.

In some embodiments, performance database 203 can include a credibility score for each specific instance of a particular machine-learning entity. For example, in one such embodiment, an AI engine may be employed to perform an autosegmentation process in target segmentation step 105, where a different instance of the AI engine is trained for a different respective region of patient anatomy. Thus, in the embodiment, performance database 203 may include a different credibility score for each instance of the AI engine that is trained to perform an autosegmentation process in target segmentation step 105.

In some embodiments, some or all credibility scores included in performance database 203 may include multiple values for each reviewer. For example, in some embodiments, such a multiple-value credibility score includes a success rate of the reviewer in detecting intentionally included errors. Alternatively or additionally, in some embodiments, a multiple-value credibility score includes a different success rate of the reviewer for each of a different category of intentionally included errors. Alternatively or additionally, in some embodiments, a multiple-value credibility score includes how recently the reviewer has had the opportunity to detect intentionally included errors. Alternatively or additionally, in some embodiments, a multiple-value credibility score includes how frequently the reviewer has had the opportunity to detect intentionally included errors. Thus, the eligibility of a particular reviewer can be based on a reviewer error detection success rate, how recently the reviewer has had the opportunity to detect intentionally included errors, how frequently the reviewer has had the opportunity to detect intentionally included errors, etc.

Error database 204 includes a plurality of previously generated errors for one or more of steps 101-110 of treatment planning process 100. Generally, each of the previously generated errors are associated with a specific one of steps 101-110 of treatment planning process 100. Thus, the errors associated with target segmentation step 105 include errors in image interpretation, such as incorrect delineations of a PTV. By contrast, errors associated with a different step of treatment planning process 100 include different types of errors. For example, the errors associated with plan optimization step 107 may include incorrectly planned beam geometries or dose distributions. In some embodiments, the previously generated errors can include human-generated errors. Alternatively or additionally, in some embodiments, the previously generated errors can include software-generated errors and/or errors extracted from actual planning treatment processes.

Planning module 205 is configured to track each radiotherapy treatment plan that includes one or more intentional errors. Thus, planning module 205 ensures that no plan that includes one or more intentional errors is delivered to a patient. In some embodiments, planning module 205 interacts with one or more planning databases 299 to indicate that a particular plan is not intended for use with any patient.

Figure 3:
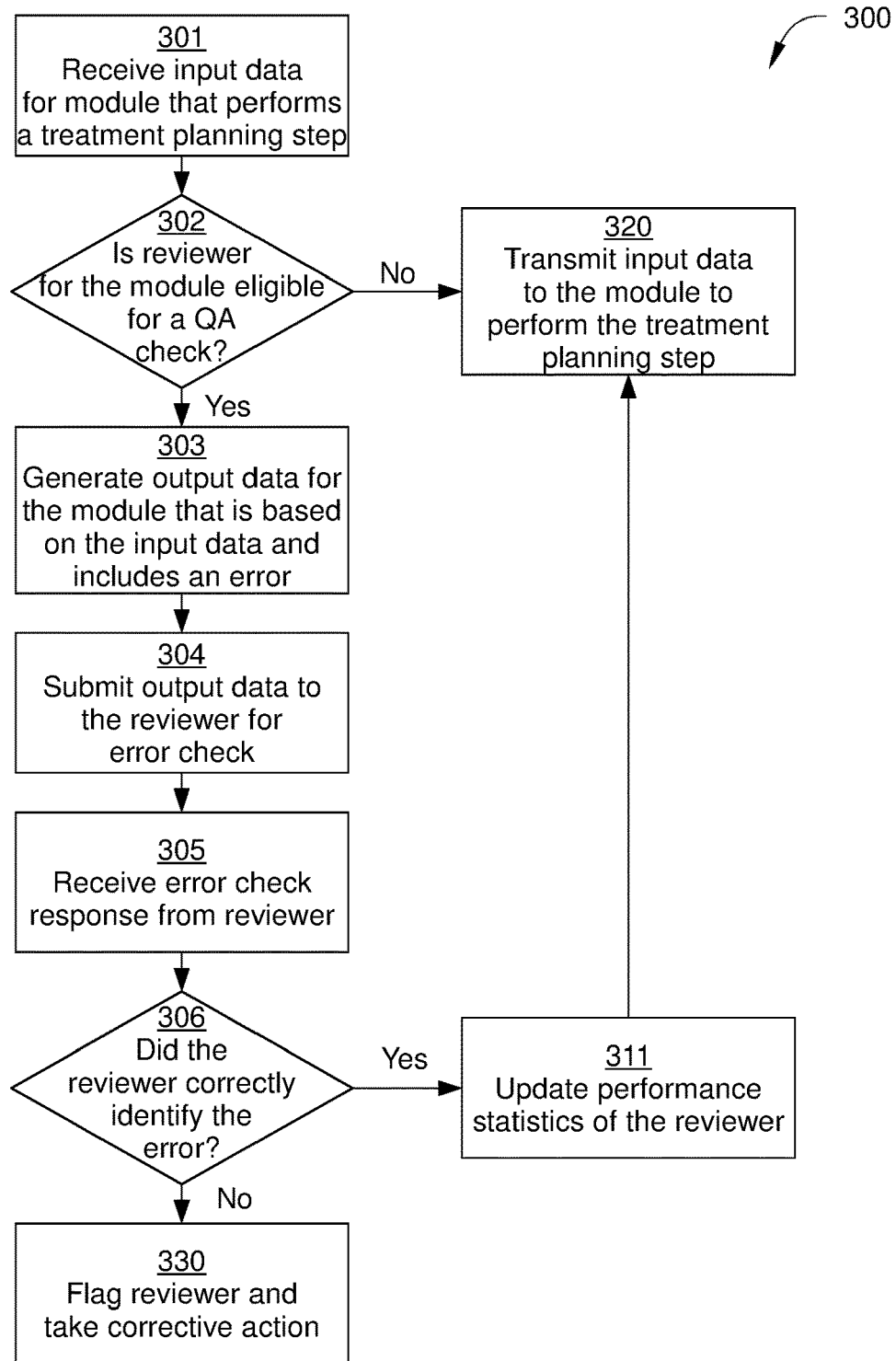
FIG. 3 sets forth a flowchart of an example quality assurance process for a treatment planning process, according to one or more embodiments of the present disclosure.

FIG. 3 sets forth a flowchart of an example QA process for a treatment planning process, according to one or more embodiments of the present disclosure. The method may include one or more operations, functions, or actions as illustrated by one or more of blocks 301-330. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with the processes and systems of FIGS. 1-2, persons skilled in the art will understand that any suitably configured QA process performed with respect to a treatment planning process is within the scope of the present disclosure.

A QA process 300 begins at step 301, when QA system 200 receives input data for a software module (the "reviewed module") that performs one of steps 101-110 of treatment planning process 100 in a automated fashion. For example, in one embodiment, input data for a reviewed module that performs target segmentation step 105 may include CT scans of a region of the anatomy of a patient and applicable information from a treatment planning directive for the patient. In another embodiment, input data for a reviewed module that performs OAR segmentation step 106 may include CT scans of the region of the anatomy of the patient, applicable information from the treatment planning directive for the patient, and delineations of one or more target regions (GTV, CTV, ITV, PTV, etc.) in the region of the anatomy. In another embodiment, input data for a reviewed module that performs plan optimization step 107 may include applicable information from the treatment planning directive for the patient and delineations of the one or more target regions (GTV, CTV, ITV, PTV, etc.) in the region. In another embodiment, input data for a reviewed module that performs quantitative plan QA step 108 may include applicable information from the treatment planning directive for the patient and one or more approved plans generated in plan optimization step 107.

In step 302, QA system 200 determines, for example via reviewer monitoring module 202, whether a reviewer for the reviewed module is eligible for a QA check. If no, QA process 300 proceeds to step 320; if yes, QA process 300 proceeds to step 303.

In step 303, QA system 200 generates output data for the reviewed module determined to be eligible for a QA check in step 302, for example via a suitable error introduction module 201. Thus, the output data so generated includes one or more intentional errors. In some embodiments, the error introduction module 201 introduces one or more intentional errors into the output of the reviewed module. In other embodiments, in lieu of the reviewed module generating output data, the error introduction module 201 generates output data that includes one or more intentional errors.

In step 304, QA system 200 submits the output data generated in step 303 to the reviewer. Generally, QA system 200 transmits the output data to the reviewer in the same way that normal output data from the reviewed module is transmitted to the reviewer. Thus, in embodiments in which the reviewer is an expert human, QA system 200 may transmit the output data to a computing device employed by the reviewer in the review process. In such embodiments, the output data generated in step 303 is indistinguishable in content and format from normal output data from the reviewed module. In embodiments in which the reviewer is a suitably trained machine-learning entity, QA system 200 transmits the output data to the AI reviewer normally.

In step 305, QA system 200 receives an error check response associated with the reviewer. For example, in embodiments in which the reviewer is an expert human, QA system 200 may receive a user input indicating that one or more errors were detected by the human reviewer or that the output is error-free. In embodiments in which the reviewer is a suitably trained machine-learning entity, QA system 200 may receive a signal from the machine-learning entity indicating that one or more errors were detected or that the output is error-free. In some embodiments, the error check response may further include information indicating the nature of the one or more errors that were detected, such as the type, severity, and/or location of the error(s) detected.

In step 306, QA system 200 determines whether the reviewer correctly identified the one or more errors. If yes, QA process 300 proceeds to step 311; if no, QA process 300 proceeds to step 330.

In step 310, which is performed in response to QA system 200 determining that the reviewer correctly identified the one or more errors, QA system 200 updates the credibility score and/or other performance statistics associated with the reviewer in performance database 203. QA process 300 then proceeds to step 320 and terminates.

Step 320 is performed in response to QA system 200 determining (1) that the reviewer for the reviewed module is not eligible for a QA check, or (2) that the reviewer for the reviewed module correctly identified the one or more intentional errors. In step 320, QA system transmits the input data received in step 301 to the reviewed module to perform the treatment planning step normally. QA process 300 then terminates.

Step 330 is performed in response to QA system 200 determining that the reviewer has not correctly identified all of the intentional errors included in the output of the reviewed module. In step 330, QA system 200 flags the reviewer and takes one or more corrective actions. For example, in embodiments in which the reviewer is an expert human, the corrective action may include updating a credibility rating of the user and modifying an appropriate value stored in performance database 203. Alternatively or additionally, in some embodiments, the corrective action may include causing an indication to be displayed informing the reviewer that the reviewer failed to detect at least one error. As a result of such corrective actions, the current performance of the reviewed module is tracked and future performance of the reviewer can be improved.

In embodiments in which the reviewer is a machine-learning process, QA system 200 may generate, as a corrective action, an identifier that is associated with the machine learning process, where the identifier indicates that the machine learning process is eligible for retraining. In such embodiments, the identifier may further indicate that the machine learning process is ineligible for use until retrained. Alternatively or additionally, in some embodiments, the corrective action may include updating a credibility rating of the current instance of the machine-learning process and modifying an appropriate value stored in performance database 203. Alternatively or additionally, in some embodiments, the corrective action may include the retraining or modification of the machine-learning process based on the one or more errors that the machine-learning process failed to detect. As a result of such corrective actions, the future performance of the machine-learning process can be improved based on increasingly subtle errors in the output of the reviewed module. For example, in some embodiments, the machine-learning process can be retrained (as well as initially trained) as a discriminator function of a GAN. One such embodiment is described below in conjunction with FIG. 4.

Figure 4:
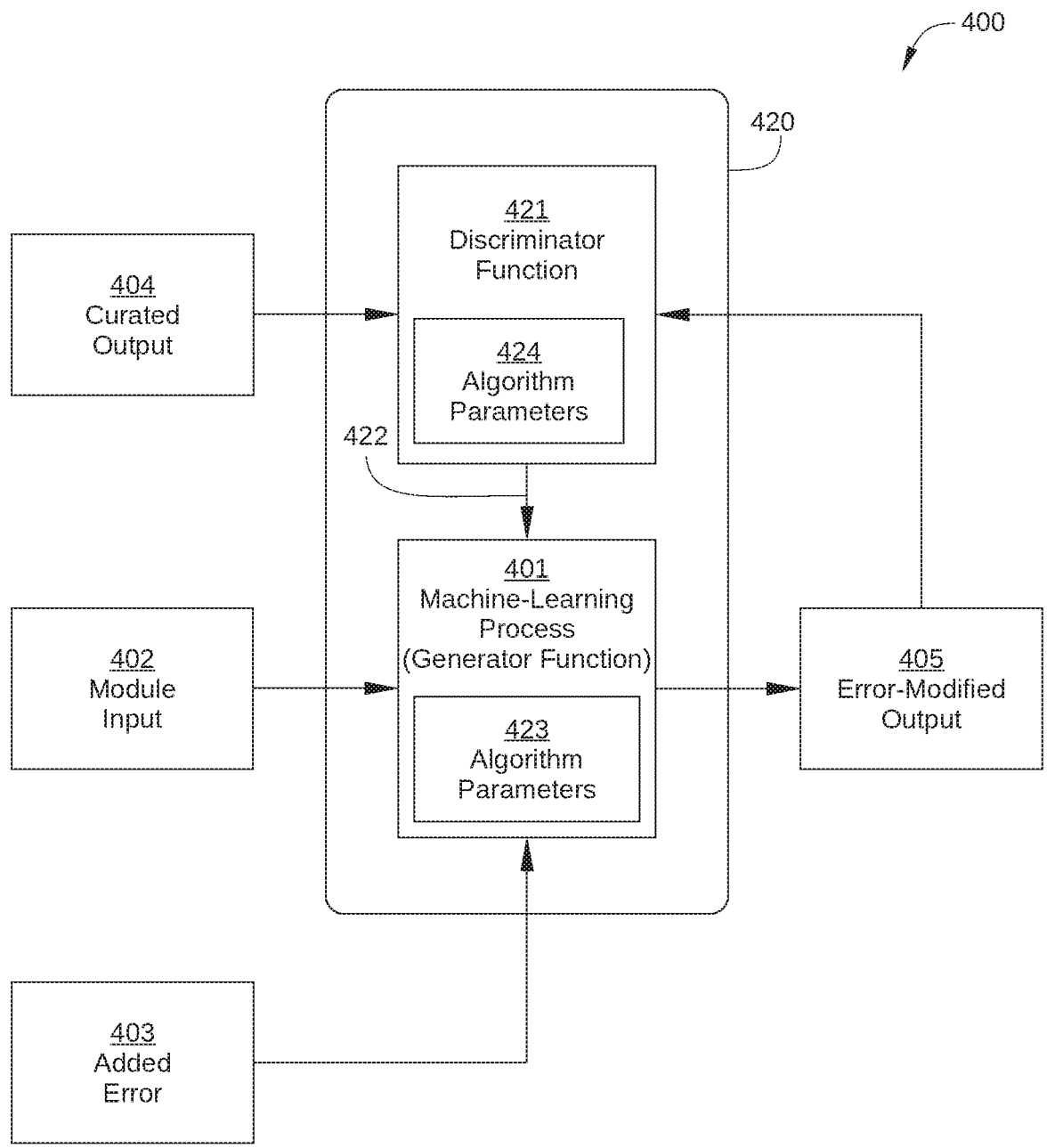
FIG. 4 is a block diagram illustrating a training process 400 for training a machine-learning process 401, according to various embodiments of the present disclosure.

FIG. 4 is a block diagram illustrating a training process 400 for training a machine-learning process 401, according to various embodiments of the present disclosure. Training process 400 includes one or more input objects (module input 402 and an added error 403) and an expected output (curated output 404). In training process 400, the one or more input objects are employed as inputs for training machine-learning process 401, which acts as a generator function of a GAN 420. In addition, the expected output (curated output 404) is employed as an input for a discriminator function 421 of GAN 420.

During GAN-training of machine-learning process 401, machine-learning process 401 learns to generate error-modified output 405. Error-modified output 405 is similar to the output of a reviewed module that performs a specific step of treatment planning process 100, except that error-modified output 405 also includes one or more intentional errors (such as added error 403). Thus, after such training, machine-learning process 401 can be employed in QA system 200 as an error introduction module 201 that is configured to generate output data for a specific step of treatment planning process 100, where the output data includes at least one intentional error.

Module input 402 is employed as an input object in training process 400, and can include a typical instance of input for the reviewed module that machine-learning process 401 is being trained to emulate. Added error 403 is a specific error or error type that can potentially occur when the reviewed module performs the step of treatment planning process 100, such as incorrectly delineated structures in an OAR or target region segmentation, over/underdosed regions that can result from a treatment plan, etc. In some embodiments, added error 403 can be selected from error database 204. Curated output 404 is employed as expected output (or "ground truth") for training process 400 and is input into discriminator function 421. Because the object of training process 400 is to teach machine-learning process 401 to generate output data that includes one or more added errors 403, each curated output 404 that is input into discriminator function 421 corresponds to a specific instance of module input 402 and a specific added error 403 that has been incorporated into that instance of module input 402. In addition, each curated output 404 includes a different error that can ordinarily occur in the output from the reviewed module. Thus, each curated output 404 enables machine-learning process 401 to learn to include a different error into error-modified output 405.

In some embodiments, various instances of curated output 404 and of added errors 403 are manually generated instances of errors occurring in module output 402. In some embodiments, various instances of curated output 404 and of added errors 403 are generated based on actual instances of errors that have been detected when module output 402 is processed by a human reviewer. In some embodiments, curated output 404 and added errors 403 can be based on one or more intentional errors included in the output of a reviewed module that a human or AI reviewer failed to detect during an iteration of QA process 300 in FIG. 3. In such embodiments, training process 400 is employed to retrain a specific AI reviewer. Thus, in such embodiments, intentional errors that have been shown to be difficult to detect can be employed to improve the sensitivity of the AI reviewer to such errors.

GAN 420 is a machine learning system that generally relies on unsupervised learning to attempt to approximate human logic or decision making while searching for hidden structures, patterns, or features in an input object. As such, GAN 420 includes machine-learning process 401 (as a generator function) and discriminator function 421.

Machine-learning process 401 can be a neural net or other suitable machine-learning model that is configured to generate an error-modified output 405 based on a particular module input 402. For example, machine-learning process 401 can be configured to generate an error-modified output 405 for a reviewed module that performs one of steps 101-110 of treatment planning process 100. In addition, during training process 400, machine-learning process 401 is configured to improve the quality of errors generated based on feedback 422 from discriminator function 421. For example, during training process 400, machine-learning process 401 is configured to modify algorithm parameters 423 so that discriminator function 421 fails to detect errors included in error-modified output 405. More specifically, through an iterative process included in training process 400, algorithm parameters 423 are modified. In this way, machine-learning process 401 can learn and/or be retrained to generate error-modified output 405 that includes errors that are more difficult for discriminator function 421 to detect. Machine-learning process 401 can then generate another error-modified output 405 using the newly modified values for algorithm parameters 423.

Discriminator function 421 can be a neural net or other suitable machine learning model that is configured to detect errors in a particular error-modified output 405 generated by machine-learning process 401. In some embodiments, during training process 400, discriminator function 421 is configured to improve its performance in detecting such errors. In such embodiments, discriminator function 421 may be configured to improve its performance based on a comparison of an expected output (or "ground truth") for training process 400, such as curated output 404, and a corresponding error-modified output 405. For example, during training process 400, discriminator function 421 is configured to determine whether an error-modified output 405 that corresponds to a specific instance of module input 402 is free of errors; compare the error-modified output 405 to a suitable instance of curated output 404; and, based on the comparison, modify algorithm parameters 424 so that discriminator function 421 can more effectively detect errors in subsequent output generated by the reviewed module. In addition, during training process 400, discriminator function 421 is further configured to generate feedback 422, which informs machine-learning process 401 what errors were detected in error-modified output 405. Based on feedback 422, machine-learning process 401 can modify algorithm parameters 423 and then generate another error-modified output 405 using the newly modified values for algorithm parameters 423.

Thus, via the iterative process included in training process 400, discriminator function 421 and machine-learning process 401 interact in a double feedback loop: discriminator function 421 is in a feedback loop with machine-learning process 401, where a difference between the ground truth of curated output 404 and error-modified output 405 acts as the feedback to discriminator function 421; and machine-learning process 401 is in a feedback loop with discriminator function 421, where feedback 422 acts as the feedback to machine-learning process 401.

In some embodiments, the iterative process included in training process 400 generally includes the application of certain success criteria. In some embodiments, one success criterion is that the magnitude and/or obviousness of the one or more errors included in error-modified output 405 are not detected (or are difficult to detect) by discriminator function 421, but are still clinically significant. In some embodiments, the clinical significance of an error included in error-modified output 405 can be determined based on a quantifiable dimensionality and/or numerical magnitude test, such as dose-volume histogram, relative biological effectiveness, predicted clinical outcome or side effect profile, OAR toxicity, etc.

According to various embodiments, in the training of a single machine-learning process 401, training method 400 can be employed a plurality of times. Specifically, training method 400 can be performed for a plurality of different module inputs 402 and/or added errors 403. That is, a single machine-learning process 401 can be trained with training method 400 multiple times, each time with a different module input 402, added error 403, and corresponding curated output 404.

Figure 5:
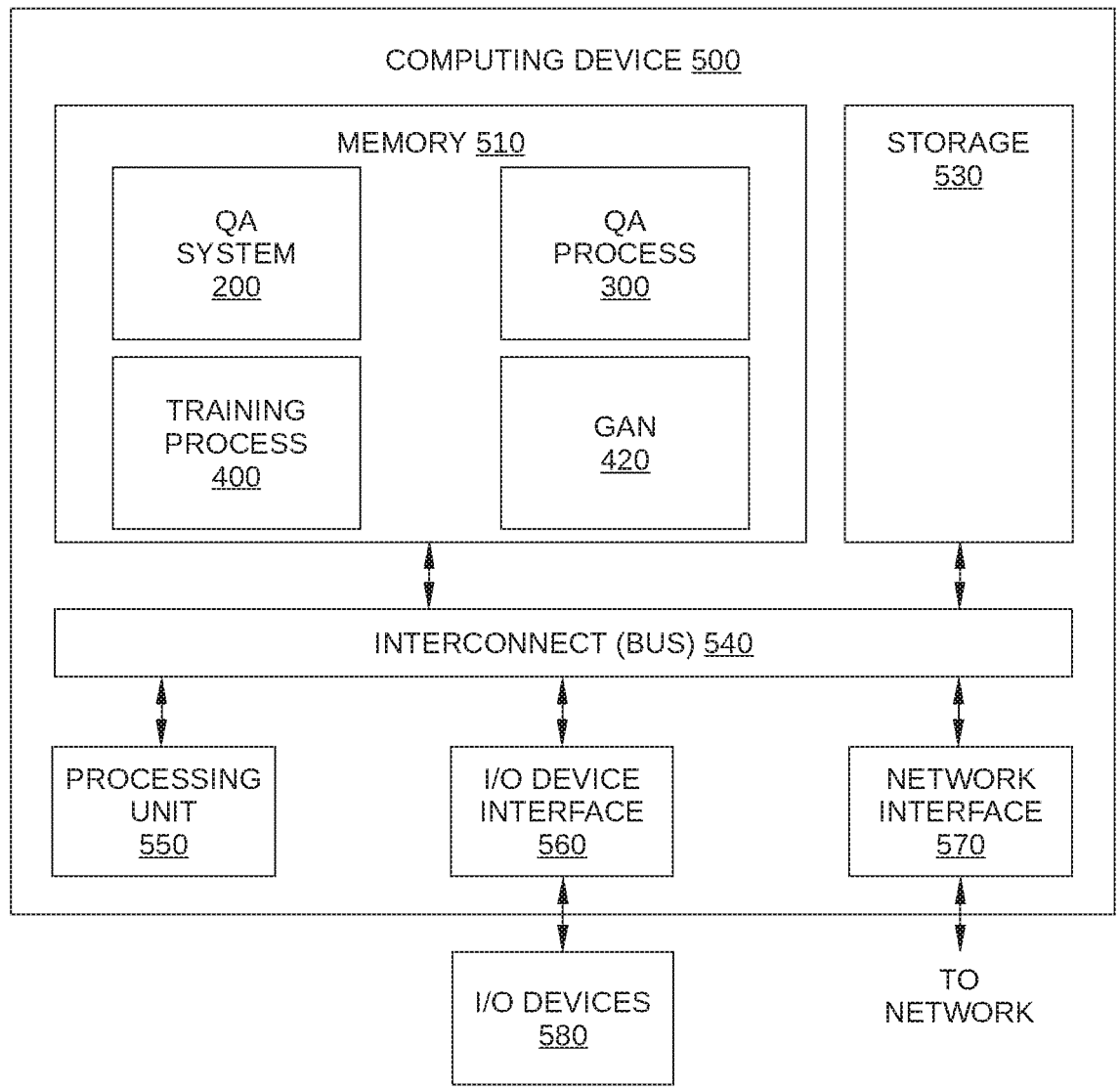
FIG. 5 is an illustration of computing device configured to perform various embodiments of the present disclosure.

FIG. 5 is an illustration of computing device 500 configured to perform various embodiments of the present disclosure. Computing device 500 may be a desktop computer, a laptop computer, a smart phone, or any other type of computing device suitable for practicing one or more embodiments of the present disclosure. In operation, computing device 500 is configured to execute QA system 200, QA process 300, training process 400, and/or GAN 420, as described herein. It is noted that the computing device described herein is illustrative and that any other technically feasible configurations fall within the scope of the present disclosure.

As shown, computing device 500 includes, without limitation, an interconnect (bus) 540 that connects a processing unit 550, an input/output (I/O) device interface 560 coupled to input/output (I/O) devices 580, memory 510, a storage 530, and a network interface 570. Processing unit 550 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 550 may be any technically feasible hardware unit capable of processing data and/or executing software applications, including QA system 200, QA process 300, training process 400, and/or GAN 420.

I/O devices 580 may include devices capable of providing input, such as a keyboard, a mouse, a touch-sensitive screen, and so forth, as well as devices capable of providing output, such as a display device and the like. Additionally, I/O devices 580 may include devices capable of both receiving input and providing output, such as a touchscreen, a universal serial bus (USB) port, and so forth. I/O devices 580 may be configured to receive various types of input from an end-user of computing device 500, and to also provide various types of output to the end-user of computing device 500, such as displayed digital images or digital videos. In some embodiments, one or more of I/O devices 580 are configured to couple computing device 500 to a network.

Memory 510 may include a random access memory (RAM) module, a flash memory unit, or any other type of memory unit or combination thereof. Processing unit 550, I/O device interface 560, and network interface 570 are configured to read data from and write data to memory 510. Memory 510 includes various software programs that can be executed by processor 550 and application data associated with said software programs, including QA system 200, QA process 300, training process 400, and/or GAN 420.

Figure 6:
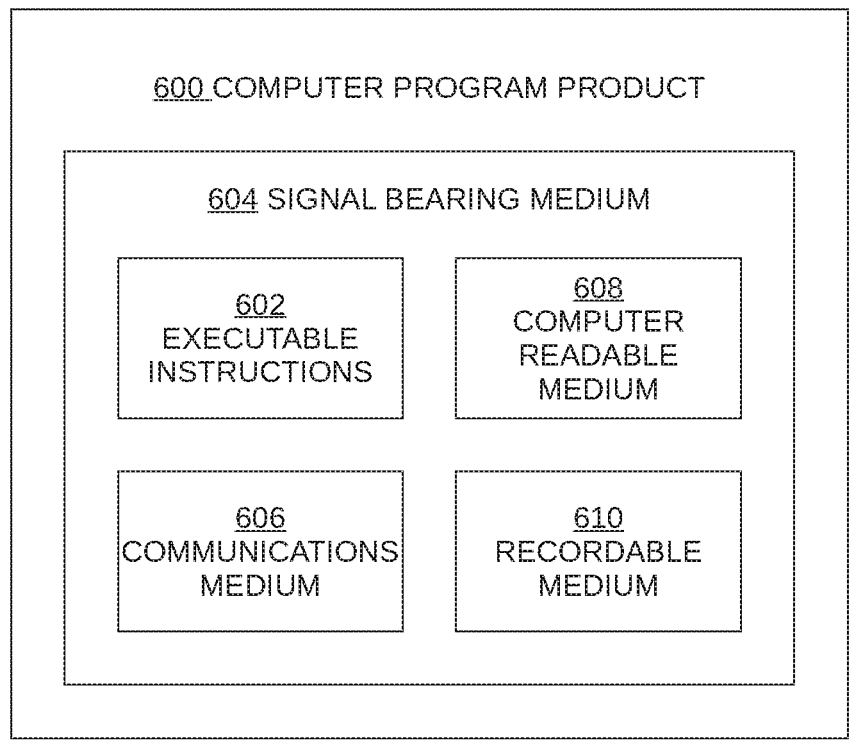
FIG. 6 is a block diagram of an illustrative embodiment of a computer program product 600 for implementing a method for segmenting an image, according to one or more embodiments of the present disclosure.

FIG. 6 is a block diagram of an illustrative embodiment of a computer program product 600 for implementing a method for segmenting an image, according to one or more embodiments of the present disclosure. Computer program product 600 may include a signal bearing medium 605. Signal bearing medium 604 may include one or more sets of executable instructions 602 that, when executed by, for example, a processor of a computing device, may provide at least the functionality described above with respect to FIGS. 1-5.

In some implementations, signal bearing medium 604 may encompass a non-transitory computer readable medium 608, such as, but not limited to, a hard disk drive, a Compact Disc (CD), a Digital Video Disk (DVD), a digital tape, memory, etc. In some implementations, signal bearing medium 604 may encompass a recordable medium 610, such as, but not limited to, memory, read/write (R/W) CDs, R/W DVDs, etc. In some implementations, signal bearing medium 604 may encompass a communications medium 606, such as, but not limited to, a digital and/or an analog communication medium (e.g., a fiber optic cable, a waveguide, a wired communications link, a wireless communication link, etc.). Computer program product 600 may be recorded on non-transitory computer readable medium 608 or another similar recordable medium 610.

In sum, embodiments of the present disclosure enables testing and evaluation of an expert human reviewer or an AI error detection engine associated with a radiotherapy treatment planning process. Intentional errors are introduced into the output of a software module or artificial intelligence (AI) engine that performs a certain step in the radiotherapy treatment planning process. The efficacy of the human or AI reviewer in detecting errors can then be evaluated or tested by determining whether the human or AI reviewer has detected the introduced error.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

I claim:

1. A computer-implemented method for quality assurance testing of a treatment planning process, the method comprising:
   receiving output data from a module of the treatment planning process, wherein the output data is based on input data for the module;
   introducing at least one intentional error into the output data;
   submitting the output data with the at least one intentional error to a reviewer for an error check, wherein the reviewer comprises a machine learning process configured to check an output of the module for errors;
   receiving an error check response associated with the reviewer; and
   when the error check response indicates a failure to detect the at least one intentional error, retraining the machine learning process based on the at least one intentional error and on normal output data from the module that is generated from the input data.

2. The computer-implemented method of claim 1, further comprising, when the error check response indicates a failure to detect the at least one intentional error, generating an identifier that is associated with the machine learning process and indicates the machine learning process is eligible for retraining.

3. The computer-implemented method of claim 1, wherein retraining the machine learning process comprises modifying the machine learning process based on the at least one error.

4. The computer-implemented method of claim 1, wherein retraining the machine learning process based on the normal output data from the module comprises processing as an expected output the normal output data with a discriminator function of the machine learning process.

5. The computer-implemented method of claim 1, wherein retraining the machine learning process based on the normal output data from the module comprises processing as an input object the output data that is based on input data for the module and includes at least one error with a generator function of the machine learning process.

6. The computer-implemented method of claim 1, wherein introducing the at least one intentional error into the output data comprises:
   retrieving the at least one intentional error from an error database; and
   incorporating the at least one intentional error into the normal output data.

7. The computer-implemented method of claim 1, wherein introducing the at least one intentional error into the output data comprises processing the normal output data with a machine learning process configured to incorporate a suitable error into output data from the module.

8. The computer-implemented method of claim 7, wherein processing the normal output data with the machine learning process comprises processing the normal output data with a generator function of the machine learning process.

9. The computer-implemented method of claim 1, wherein introducing at least one intentional error into the output data comprises:
   receiving the input data for the module; and
   generating the output data by processing the input data with an error-generating module instead of with the module of the treatment process.

10. The computer-implemented method of claim 9, wherein the error-generating module comprises a machine learning process configured to generate the output data with an error associated with the module of the treatment planning process.

11. The computer-implemented method of claim 1, further comprising, when the error check response indicates the reviewer detected the at least one intentional error, updating a credibility rating of the user.

12. A non-transitory computer-readable storage medium including instructions that, when executed by one or more processors, configure the one or more processors to perform the steps of:
   receiving output data from a module of the treatment planning process, wherein the output data is based on input data for the module;
   introducing at least one intentional error into the output data;
   submitting the output data with the at least one intentional error to a reviewer for an error check, wherein the reviewer comprises a machine learning process configured to check an output of the module for errors;
   receiving an error check response associated with the reviewer; and
   when the error check response indicates a failure to detect the at least one intentional error, retraining the machine learning process based on the at least one intentional error and on normal output data from the module that is generated from the input data.

13. The non-transitory computer-readable storage medium of claim 12, further including instructions that, when executed by one or more processors, configure the one or more processors to perform the step of, when the error check response indicates a failure to detect the at least one intentional error, generating an identifier that is associated with the machine learning process and indicates the machine learning process is eligible for retraining.

14. The non-transitory computer-readable storage medium of claim 12, wherein retraining the machine learning process comprises modifying the machine learning process based on the at least one error.

15. The non-transitory computer-readable storage medium of claim 12, wherein retraining the machine learning process based on the normal output data from the module comprises processing as an expected output the normal output data with a discriminator function of the machine learning process.

16. The non-transitory computer-readable storage medium of claim 12, wherein retraining the machine learning process based on the normal output data from the module comprises processing as an input object the output data that is based on input data for the module and includes at least one error with a generator function of the machine learning process.

17. The non-transitory computer-readable storage medium of claim 12, wherein introducing the at least one intentional error into the output data comprises:
retrieving the at least one intentional error from an error database; and
incorporating the at least one intentional error into the normal output data.

18. The non-transitory computer-readable storage medium of claim 12, wherein introducing the at least one intentional error into the output data comprises processing the normal output data with a machine learning process configured to incorporate a suitable error into output data from the module.

19. The non-transitory computer-readable storage medium of claim 12, wherein introducing at least one intentional error into the output data comprises:
receiving the input data for the module; and
generating the output data by processing the input data with an error-generating module instead of with the module of the treatment process.

20. The non-transitory computer-readable storage medium of claim 12, wherein the error-generating module comprises a machine learning process configured to generate the output data with an error associated with the module of the treatment planning process.

* * * * *